(12) United States Patent
Griggio et al.

(10) Patent No.: US 12,390,092 B2
(45) Date of Patent: Aug. 19, 2025

(54) CONFOCAL EYE FUNDUS SCANNING SYSTEM

(71) Applicant: LUNEAU TECHNOLOGY OPERATIONS, Pont-de-l'Arche (FR)

(72) Inventors: Paola Griggio, Padua (IT); Matteo Manente, Scorzè (IT); Flavio Rizzardi, Albignasego (IT); Michele Martin, Montegrotto Terme (IT)

(73) Assignee: LUNEAU TECHNOLOGY OPERATIONS, Pont-de-l'Arche (FR)

( * ) Notice: Subject to any disclaimer, the term of this patent is extended or adjusted under 35 U.S.C. 154(b) by 356 days.

(21) Appl. No.: 18/322,836

(22) Filed: May 24, 2023

(65) Prior Publication Data

US 2023/0380671 A1    Nov. 30, 2023

(30) Foreign Application Priority Data

May 25, 2022  (FR) ...................................... 2205067

(51) Int. Cl.
*A61B 3/10*    (2006.01)
*A61B 1/00*    (2006.01)
*A61B 3/12*    (2006.01)

(52) U.S. Cl.
CPC ........ *A61B 1/00172* (2013.01); *A61B 3/1025* (2013.01); *A61B 3/12* (2013.01)

(58) Field of Classification Search
CPC ..... A61B 1/00172; A61B 3/1025; A61B 3/12; A61B 3/13; A61B 3/10; A61B 90/08
See application file for complete search history.

(56) References Cited

U.S. PATENT DOCUMENTS

| | | |
|---|---|---|
| 2015/0272434 A1 | 10/2015 | Satake et al. |
| 2019/0000316 A1 | 1/2019 | Hirose et al. |
| 2020/0000336 A1 | 1/2020 | Bublitz et al. |
| 2020/0077889 A1 | 3/2020 | Fukuma et al. |

FOREIGN PATENT DOCUMENTS

| | | |
|---|---|---|
| EP | 1872713 A1 | 1/2008 |
| EP | 1875857 A1 | 1/2008 |
| EP | 3235421 A1 | 10/2017 |
| FR | 3112866 A1 | 1/2022 |

OTHER PUBLICATIONS

France Search Report dated Jan. 11, 2023 from Application No. FR2205067.

*Primary Examiner* — Towfiq Elahi
(74) *Attorney, Agent, or Firm* — INNOVATION CAPITAL LAW GROUP, LLP; Vic Lin

(57) ABSTRACT

A confocal fundus scanner that includes—a lighting device (11) for generating one light beam; a detector (12) for forming a digital image on the basis of received signals; optical units (131, 132, 133, 134, 135, 136) positioned to make light beam passing through them to direct it along an illumination path (A) to a target position (O) and to send a reflection back to the detector (12) along an image path (B); —a scanning device (14) having a movable wall (141) with a first slot (142) which is positioned to intercept the image path (B) and a second slot (143) positioned to intercept the illumination path (A). The slots (142, 143) are configured and positioned to move simultaneously and to shape the light beams in linear cross-section light blades.

20 Claims, 4 Drawing Sheets

CONFOCAL EYE FUNDUS SCANNING SYSTEM

TECHNICAL FIELD

The present invention relates to a confocal fundus scanner, i.e. a confocal optical device capable of reconstructing a real colour image of the fundus by scanning.

The device is configured to project a beam of white light capable of intercepting the eye fundus in an illuminated segment. The beam is directed in such a way that the illuminated segment is displaced on the eye fundus transversely to its development. Reflected images of the segment illuminated by the displaced channel on the fundus are acquired to reconstruct the image of the fundus.

The device according to the present invention is structurally simpler and more robust than conventional devices and allows reliable and accurate acquisition of the fundus.

STATE OF THE ART

Today, in the field of fundus image acquisition, the technique of "widefield imaging" is well known. Another current technique includes the use of confocal scanning laser ophthalmoscopy (cSLO).

In widefield imaging, the retina is illuminated by a flash and a two-dimensional photograph is acquired. This technique presents the problem of eliminating reflexes generated by the cornea and those generated by the lens surfaces. Furthermore, these traditional devices have the advantage of allowing rapid acquisition of images of the retina, thus avoiding the effects of movement. They also provide high lateral resolution with high signal level and dynamic range.

In addition, the widefield imaging technique has severe limitations due to the need to eliminate effects, limiting the field of view to about 60 degrees and making it more difficult to combine with other techniques. In addition, the entire field of view of the imaging system is used at the same time.

In contrast, point-scanning devices involve illuminating a small spot on the retina with a laser and detecting the reflected or emitted light (e.g. in the case of fluorescence) through a detector with a pinhole in front of the detector. The pinhole is optically combined with the illuminated spot on the retina so that stray light and out-of-focus objects are removed from the image. To reconstruct the image of the entire retina, the spot is moved or scanned.

These kinds of devices, called confocal scanners, have the advantage of removing the out-of-focus light, thus showing high contrast images, but they have some limitations.

In particular, they require the use of spotlighting, therefore they involve the use of lasers or SLD, which are expensive, and create a high instantaneous light intensity on the eye, to the detriment of patient safety.

However, the optic disc is dark because it is not in the focal plane of the retina.

In addition, the image of each point is acquired in sequence, therefore a very high speed scan of the fundus is required to avoid motion artefacts, at the expense of structural simplicity and cost of the device.

In addition, due to the high speed of acquisition required, traditional equipment of this type has high frequency vibrations and is noisy.

Another current technique is the line scan of the eye fundus.

This technique illuminates a linear segment rather than a point on the retina, thus increasing the area scanned and therefore requiring lower scan speeds to limit image defects due to motion artefacts.

These systems maintain high suppression of reflexes and image pollution from out-of-focus objects, thanks to the confocal structure.

The width of the scan line can be adapted to the amount of off-field light suppression required.

However, the line-scanning technique currently used has its limitations. For example, variations in the intensity of the line or the sensitivity of the linear structure for image acquisition can cause streaks in the acquired image.

Today, this technique requires the use of a mask to eliminate the reflection of stray surfaces, such as the surface of the cornea, as well as those of the lenses of the optical system, which compromise the optical efficiency of the system and result in dark images.

In addition, the formation of the illuminated segment on the retina is now achieved by using a galvanometric scanner which is fragile and expensive.

As an alternative to the galvanometric scanner, there are masks with a slot in front of the light source and the image acquisition sensor.

To conduct the scan, the masks are moved relative to the light source and the sensor, or conversely, the sensor and/or the light source are moved relative to the masks.

However, this alternative requires high motion synchronization to obtain good quality images, at the expense of the structural simplicity and robustness of the device.

In addition, this solution requires very precise alignment of the masks during construction, where the slots must be aligned to the micrometre. This alignment can also be re-established to compensate for a degradation of the mutual positions resulting from the use of the device.

In addition, traditional solutions with galvanometric scanners and moving masks tend to make vibrations or noise perceptible and can be particularly annoying.

On the other hand, there is a major criticism associated with the possibility of mask soiling, which can significantly compromise the quality of the image acquired with these traditional devices.

SUMMARY OF THE INVENTION

The problem underlying the present invention is therefore enabling a fundus analysis that avoids vibrations and noise by means of a simpler and more robust device than traditional techniques.

The task of a confocal fundus scanner according to the present invention is therefore to solve this problem.

In the context of this task, the aim of the disclosure is to create a confocal fundus scanner that allows for easier and more accurate fundus scanning than traditional solutions.

A further aim of the invention is to provide a confocal fundus scanner for acquiring an image of the fundus by scanning the fundus while avoiding partial or total signal loss or, in any case, an excessive signal-to-noise ratio in order to achieve high image acquisition efficiency.

Another aim of this invention is to develop a confocal fundus scanner that allows for greater stability of operation over time by reducing the possible maintenance requirements to restore optimal signal-to-noise ratios or image brightness.

A further aim of the invention is to achieve a confocal fundus scanner that requires fewer and simpler maintenance, to the benefit of its productivity.

In the context of this task, the aim of the invention is to create a confocal fundus scanner that is easy to produce using known production technologies.

Another aim of the present invention is to provide a confocal fundus scanner that is structurally simple and easy to use.

This task, aim and other aims which will become more apparent later, are achieved by the confocal fundus scanner according to the attached independent claim.

Detailed features of a confocal fundus scanner according to the invention are set out in the dependent claims.

Further features and advantages of the disclosure will be set out below in the description of a preferred, but not exclusive, embodiment of a confocal fundus scanner according to the invention, which is illustrated by way of non-limiting example in the drawing tables below.

DETAILED DESCRIPTION

Figure 1:
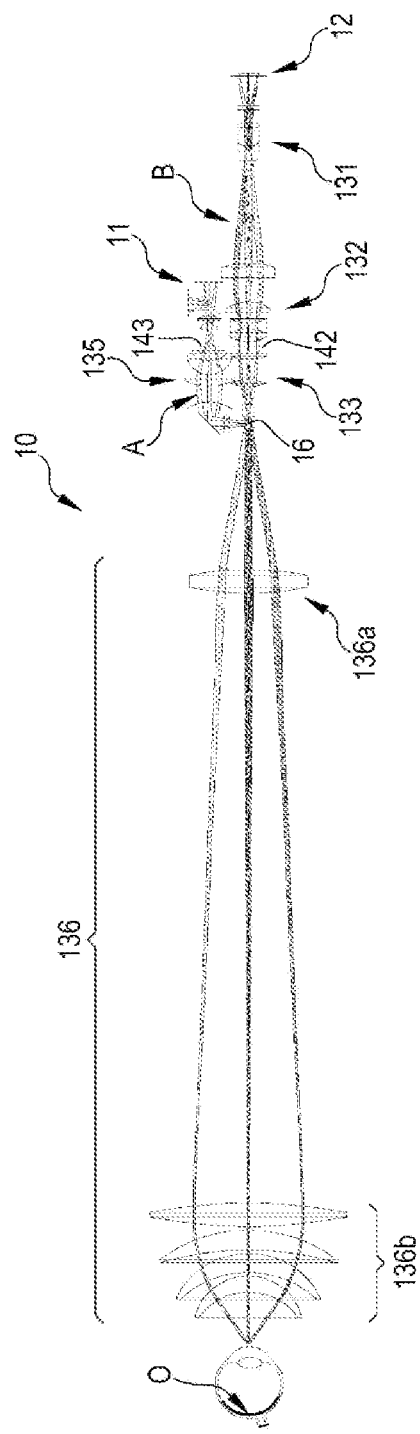
FIG. 1 shows a simplified diagram of a confocal fundus scanner according to the invention.
Figure 2:
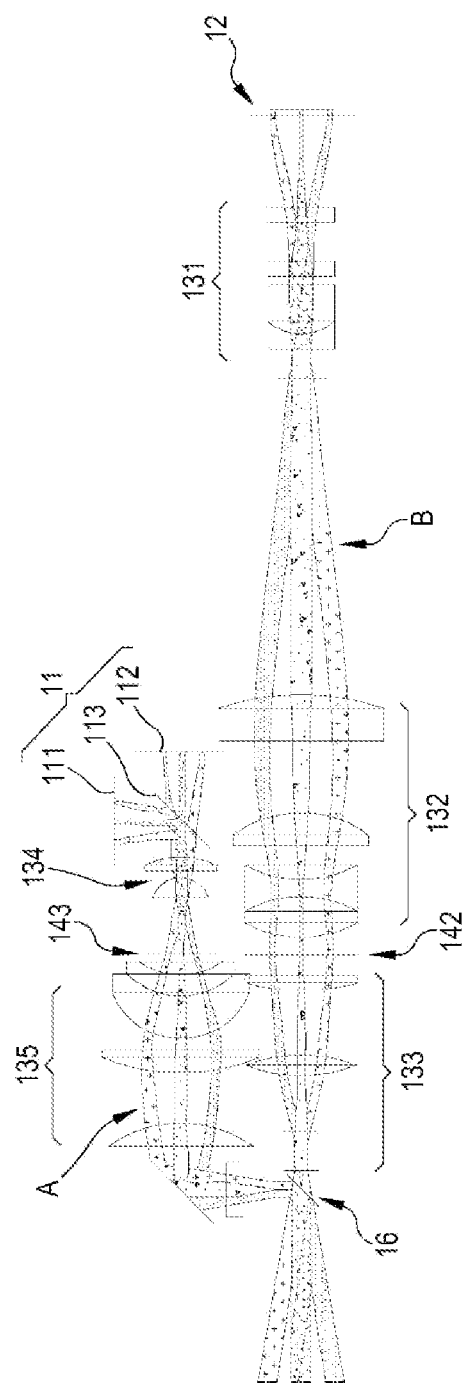
FIG. 2 shows a particular enlargement of the simplified diagram in FIG. 1.

In particular, in FIG. 1, a confocal fundus scanner is globally indicated by the reference number 10 and comprises:

- a lighting device 11 configured to generate at least one light beam;
- a detector 12 capable of emitting a signal when struck by light to form a digital image;
- optical groups 131, 132, 133, 134, 135, 136 positioned with respect to the lighting device 11 and the detector 12 so as to be traversed by the light beam to direct it along an illumination path A towards a predefined target position O and to send a reflection of this light beam from the target position O towards the detector 12 along an image path B;
- a scanner 14 having a movable wall 141 with a first slot 142 which is positioned to intercept image path B and a second slot 143 positioned to intercept illumination path A.

The second slot 143 is configured and positioned to form an illuminating light strip with a linear cross-section from the light beam.

The first slot 142 is configured and positioned so as to form, by reflection, a strip of reflected light with a linear cross section.

The first slot 142 and the second slot 143 are in positions relative to the target position O, so as to be corresponding to the retina of the patient's eye, under conditions of use.

The optical groups 131, 132, 133, 134, 135, 136 can be configured to optically combine the first slot 142 and the second slot 143 with the target position O.

The wall 141 is configured such that, as a result of a movement of the wall 141, the first slot 142 and the second slot 143 are displaced in an interlocking manner.

In other words, the wall 141 has the first slot 142 and the second slot 143 which are monolithically movable with the wall 141, for example they may be made of two parts of the wall 141 which are monolithically attached to each other, or which are integral, i.e. they form a unitary body.

This allows the fundus to be scanned while avoiding or greatly reducing the noise and/or vibration generated by traditional devices.

Figure 3:
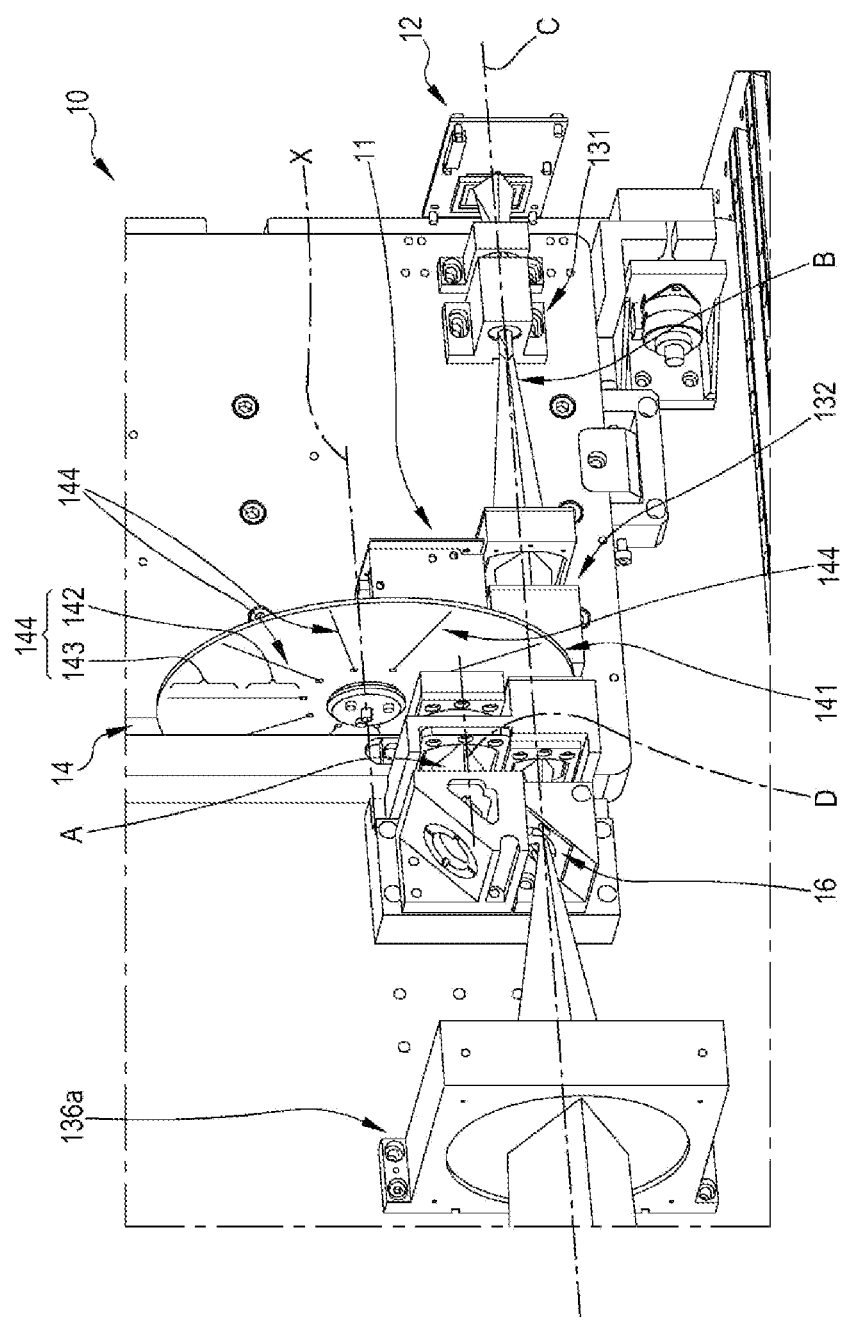
FIG. 3 and FIG. 4 show two different perspective views of an embodiment of a fundus scanner according to the invention.
Figure 4:
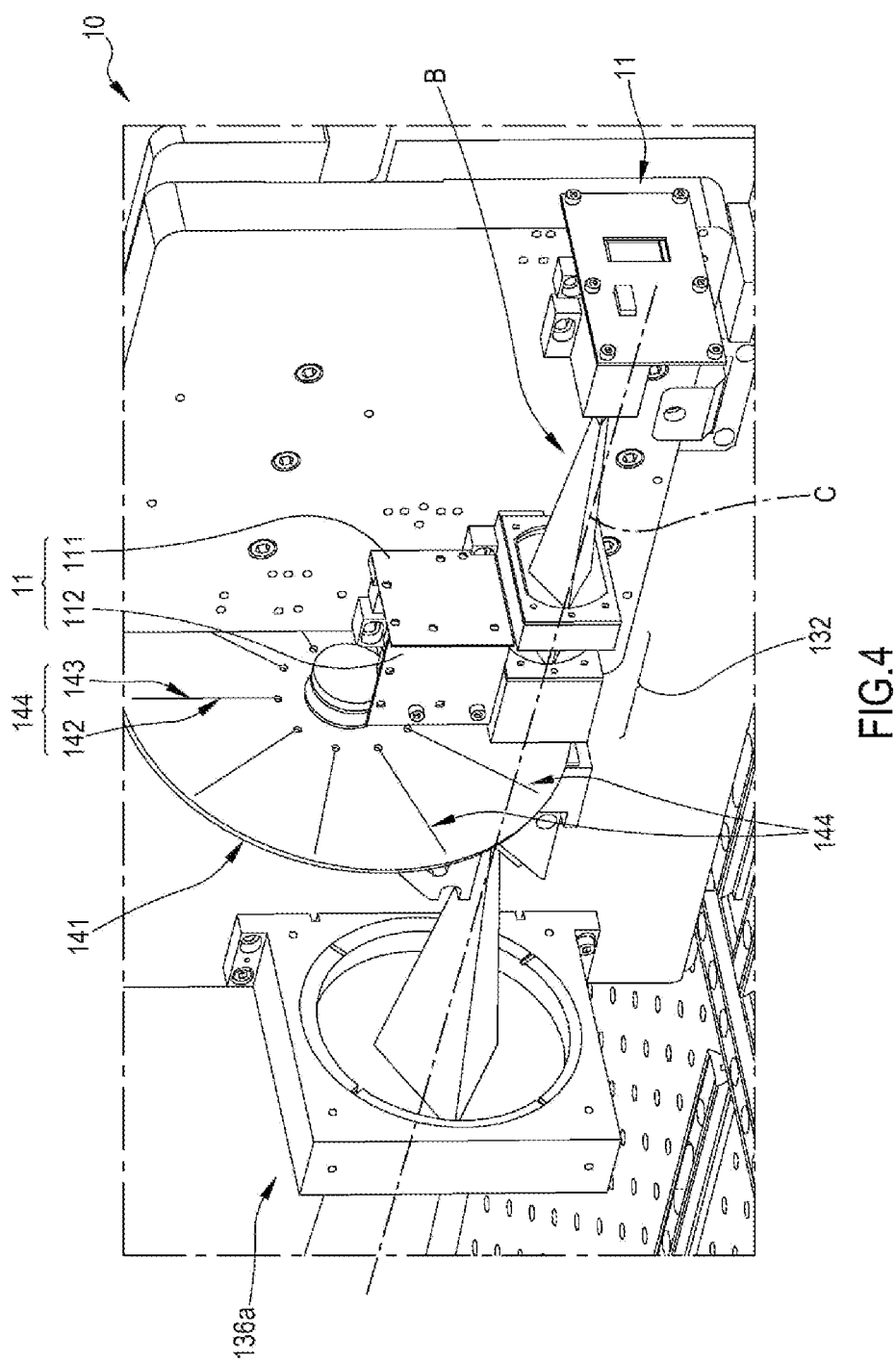

In particular, as shown in FIGS. 3 and 4, the first slot 142 and the second slot 143 are mutually integral and are respective parts of a single slot, which in FIGS. 3 and 4 for simplicity is indicated by reference 144.

The wall 141 may rotate about an axis of rotation X, for example to allow the passage of the first slot 142 and the second slot 143 to intercept or intersect the illumination path A and the image path B, respectively, in a cyclic manner. In this way, it is possible to obtain a particularly strong structure with wall 141 intercepting image path B and illumination path A and, by rotating, forming the illuminated light strip and the reflected light strip when the first slot 142 and the second slot 143 intersect the illumination path A and the image path B respectively.

The speed of rotation of the wall 141 can be fixed or adjustable and can be set to define the scanning speed, i.e. the speed at which the illuminating light strip travels across the fundus placed, in use, in the target position O.

For example, as shown in FIGS. 3 and 4, the wall 141 may have multiple unitary slots 144, or separated first and second slots if they are not integral, i.e. forming a single slot.

Clearly, the radial dimensions of the wall 14, relative to the axis of rotation X, can be chosen according to the size of the lighting device 11 and the detector 12 that will face the wall 141.

In particular, the wall 141 may be a thin disc wedged on the axis of an electric motor 145.

The lighting device 11 may comprise:

- a first light source 111, comprising for example an array of leds, capable of emitting light in the visible field, preferably white, to perform the imaging function;
- a second light source 11 configured to emit light radiation not located in the visible field, for example infrared radiation, and configured to generate targets in the target position O, with the scanner 10 being configured to allow a retina to be photographed in the target position O, if necessary automatically;
- a reflecting body configured to route the light rays emitted by the first 111 and second 112 light sources along the illumination path A.

The illumination path A and the image path B may be aligned along a plane to which the axis of rotation X belongs if the first slot 142 and the second slot 143 extend in a radial direction with respect to the axis of rotation X, so as to obtain a precise interception of the second slot 143 by the reflection of the light beam, filtered by the first slot 142, and reflected by the target position O.

The optical groups 131, 132, 133, 134, 135 and 136 are configured so as to define a first optical axis C along which the illumination path A intercepts the wall 141 and a second optical axis D along which the illumination path A intercepts the wall 141.

The axis of rotation X may be parallel to the first and second optical axes D as they intercept the wall 141 and the first and second slots 142 and 143.

The first optical axis C may be parallel to the second optical axis D as they intercept the wall 141 and the first and second slots 142 and 143 and they may be located on the same plane as the axis of rotation X in order to have optimal synchronisation, in action, between the interaction of the first slot 142 with the light beam directed towards the target position O, and the interaction between the reflection of the light beam coming from the target position O and the second slot 143, in order to achieve optimal acquisition of an image of the fundus placed at the target position O.

In a preferred embodiment of the present invention, for reasons of simplicity and robustness of construction, the first slot 142 and the second slot 143, or the unitary slot 144 if these form two parts, develop in a direction of development which is radial to the axis of rotation X.

However, in general, the axis of rotation X can be warped with respect to the optical axes C and D, and the wall can have different shapes.

For example, in an embodiment not shown in the accompanying figures, the wall could be frustoconical in shape and the first slot and the second slot may extend along a plane radial to the axis of rotation of said wall.

The axis of rotation could be inclined with respect to the first and second optical axes at an angle equal to that of the opening of the conical sheet on which the wall develops so that when intercepting the first and second optical axes, the first and second slots extend perpendicularly to them.

In another possible embodiment of the present invention, the wall could develop along a surface that is, for example, cylindrical, coaxial with the axis of rotation and perpendicular to said first and second optical axes.

In this case, the first slot and the second slot can develop in a direction of development that is parallel to the axis of rotation.

The wall could in turn be cylindrical and the lighting and sensor could be surrounded by it.

This embodiment would be smaller in size in the direction perpendicular to the first and second optical axes but certainly larger transversely, compared to the other embodiments described above.

Optical groups 131, 132, 133, 134, 135 and 136 may include:
- a first optical group 131, facing the detector 12 and configured to compensate for optical aberrations;
- a second optical unit 132 following the first optical unit and configured to create an image of a retina present at the target position O, on the detector 12;
- a third optical unit 133 configured to conjugate the patient's retina, namely the target position O, with the second slot 143;
- a fourth optical unit 134 configured to condense light produced by the lighting device 11 onto the first slot 142;
- a fifth optical unit 135 configured to conjugate the patient's retina, namely the aim position O with the first slot 142;
- a sixth optical unit 136 comprising a scanning lens 136a and a target unit 136b configured to create a combined pupil and retina point.

The device 10 according to the present invention may include an optical body 16 adapted to separate the image path B from the illumination path A and which, for example, may comprise a perforated mirror so that the illumination path
A intercepts a specular surface of this perforated mirror which is annular to an aperture which is crossed by the image path B, it is thus possible to ensure a high cleaning of the fundus image.

For example, a perforated mirror as described above is particularly useful for obtaining wide field imaging.

In other embodiments of the present invention, the perforated mirror may provide multiple holes, possibly diffusely distributed.

The optical body 16 may be in a position optically associated with the pupil of the eye to be scanned where the position of the retina is in the target position O.

It is understood, therefore, that a confocal fundus scanner according to the present invention achieves the mandated task and aims by providing a structured solution that is more reliable and robust than currently known solutions.

In particular, a confocal fundus scanner allows the acquisition of an image of the fundus by scanning the fundus with full synchronization between the illuminating light strip and the light strip that constitutes the reflection of the fundus, in particular by allowing a very clean image to be obtained by the light reflected by the surfaces of the lenses of the optical groups as well as the cornea.

In addition, a confocal fundus scanner requires fewer and simpler maintenance interventions, which benefits its productivity, as it does not require re-alignment of the slots as they are made in a single body or monolithic manner.

The confocal fundus scanner according to the present invention is, moreover, easily achievable with known production technologies.

The invention thus designed is susceptible to numerous modifications and variants, all of which fall within the protection of the accompanying claims.

In addition, all of the details may be replaced by other technically equivalent elements.

Where the operational features and techniques mentioned are followed by reference signs or numbers, these reference signs or numbers have been affixed for the sole purpose of increasing the intelligibility of the description and the claims themselves and therefore do not in any way restrict the interpretation of each element identified, merely by way of example, by these reference signs or numbers.

The invention claimed is:

1. A confocal fundus scanner, comprising:
   a lighting device configured to generate at least one light beam;
   a detector capable of emitting a signal when struck by light to form a digital image;
   optical units positioned with respect to the lighting device and the detector so as to have the light beam passing therethrough to direct it along an illumination path towards a predefined target position and to send a reflection of that light beam from the target position towards said detector along an image path; and
   a scanning device with a movable wall with a first slot positioned to intercept said image path and a second slot positioned to intercept said illumination path wherein:
   the first slot is configured and positioned to form from said light beam an illumination light strip with a linear section;
   the second slot is configured and positioned so as to form from said reflection a strip of reflected light having a linear section; and
   the wall is configured such that as a result of their own movement, the first and second slots are jointly displaced.

2. The scanner according to claim 1, wherein the first slot and second slot of the scanning device are mutually integral and are respective parts of a unitary slot.

3. The scanner according to claim 1, wherein the wall rotates about an axis of rotation.

4. The scanner according to claim 3, wherein:
   the optical units are configured so as to define a first optical axis along which the illumination path intercepts the wall and a second optical axis along which the illumination path intercepts the wall; and the first optical axis is parallel to the second optical axis.

5. The scanner according to claim 3, wherein the axis of rotation is parallel to the first and second optical axes.

6. The scanner according to claim 3, wherein slot and second slot develop in a direction of development radial to the axis of rotation.

7. The scanner according to claim 6, wherein the wall is disc-shaped and wedged on an axis of an electric motor which defines the axis of rotation.

8. The scanner according to claim 3, wherein the axis of rotation is perpendicular to the first and second optical axes.

9. The scanner according to claim 3, wherein the first slot and second slot develop in a direction of development which is parallel to the axis of rotation.

10. The scanner according to claim 9, wherein the wall extends along a cylindrical or frustoconical surface.

11. The scanner according to claim 2, wherein the wall rotates about an axis of rotation.

12. The scanner according to claim 11, wherein:

the optical units are configured so as to define a first optical axis along which the illumination path intercepts the wall and a second optical axis along which the illumination path intercepts the wall (141); and the first optical axis is parallel to the second optical axis.

13. The scanner according to claim 11, wherein the axis of rotation is parallel to the first and second optical axes.

14. The scanner according to claim 11, wherein the first slot and second slot develop in a direction of development radial to the axis of rotation.

15. The scanner according to claim 12, wherein the first slot and second slot develop in a direction of development radial to the axis of rotation.

16. The scanner according to claim 13, wherein the first slot and second slot develop in a direction of development which is radial to the axis of rotation.

17. The scanner according to claim 11, wherein the wall is disc-shaped and wedged on an axis of an electric motor which defines the axis of rotation.

18. The scanner according to claim 4, wherein the first slot and second slot develop in a direction of development which is parallel to the axis of rotation.

19. The scanner according to claim 6, wherein the first slot and second slot develop in a direction of development which is parallel to the axis of rotation.

20. The scanner according to claim 8, wherein the wall extends along a cylindrical or frustoconical surface.

* * * * *